(12) United States Patent
Arai et al.

(10) Patent No.: US 11,371,834 B2
(45) Date of Patent: Jun. 28, 2022

(54) MEASURING DEVICE

(71) Applicant: FUJIFILM Corporation, Tokyo (JP)

(72) Inventors: Hisao Arai, Kanagawa (JP); Yi Hu, Kanagawa (JP); Ken Okada, Kanagawa (JP); Mayumi Katayama, Kanagawa (JP); Tsukasa Kitahashi, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 634 days.

(21) Appl. No.: 16/359,289

(22) Filed: Mar. 20, 2019

(65) Prior Publication Data

US 2019/0219386 A1    Jul. 18, 2019

Related U.S. Application Data

(63) Continuation of application No. PCT/JP2017/033340, filed on Sep. 14, 2017.

(30) Foreign Application Priority Data

Sep. 21, 2016  (JP) .............................. JP2016-183781

(51) Int. Cl.
*G01B 11/24* (2006.01)
*A61B 5/00* (2006.01)
*A61B 5/107* (2006.01)

(52) U.S. Cl.
CPC ............ *G01B 11/24* (2013.01); *A61B 5/0064* (2013.01); *A61B 5/1077* (2013.01); *A61B 5/1079* (2013.01); *A61B 5/444* (2013.01); *A61B 5/70* (2013.01); *A61B 5/7445* (2013.01); *A61B 2503/40* (2013.01)

(58) Field of Classification Search
None
See application file for complete search history.

(56) References Cited

U.S. PATENT DOCUMENTS

| | | | |
|---|---|---|---|
| 10,352,817 B2 | 7/2019 | May et al. | |
| 2005/0084176 A1 | 4/2005 | Talapov et al. | |
| 2008/0192246 A1* | 8/2008 | Neiss ................. | G01N 21/6458 356/301 |
| 2013/0258336 A1 | 10/2013 | Ostermeyer et al. | |

(Continued)

FOREIGN PATENT DOCUMENTS

| | | |
|---|---|---|
| DE | 102014007203 A1 | 11/2015 |
| JP | 2007-229320 A | 9/2007 |

(Continued)

OTHER PUBLICATIONS

Extended European Search Report, dated Aug. 26, 2019, for European Application No. 17852956.6.

(Continued)

*Primary Examiner* — Yi-Shan Yang
(74) *Attorney, Agent, or Firm* — Birch, Stewart, Kolasch & Birch, LLP (57) ABSTRACT

A measuring device includes a measuring unit that measures the morphology of a convex portion, and a position fixing unit that includes an opening in which the convex portion is to be disposed and a fixing member which includes the opening at a center thereof and against which the periphery of the convex portion is to be pressed. The size of the opening of the position fixing unit is capable of being changed.

12 Claims, 5 Drawing Sheets

(56) References Cited

U.S. PATENT DOCUMENTS

| 2014/0236003 A1* | 8/2014 | Hielscher | A61B 5/708 |
| | | | 600/428 |
| 2016/0054196 A1* | 2/2016 | Glasenapp | G01M 11/0214 |
| | | | 356/124 |

FOREIGN PATENT DOCUMENTS

| JP | 2013-161133 A | 8/2013 |
| JP | 2014-240793 A | 12/2014 |
| JP | 2014240793 A * | 12/2014 |

OTHER PUBLICATIONS

International Preliminary Report on Patentability and Written Opinion of the International Searching Authority (Forms PCT/IB/326, PCT/IB/373 and PCT/ISA/237) for International Application No. PCT/JP2017/033340, dated Apr. 4, 2019, with English translation.
International Search Report (Form PCT/ISA/210) for International Application No. PCT/JP2017/033340, dated Dec. 5, 2017, with English translation.
Japanese Notice of Reasons for Refusal for Japanese Application No. 2016-183781, dated May 7, 2019, with English translation.
Object Management Group, "OMG Unified Modeling Language™ (OMG UML)," Version 2.5, Mar. 2015, URL:http://www.omg.org/spec/UML/2.5, pp. 1-546 (588 pages total).

* cited by examiner

MEASURING DEVICE

CROSS-REFERENCE TO RELATED APPLICATIONS

This application is a continuation application of International Application No. PCT/JP2017/033340, filed Sep. 14, 2017, the disclosure of which is incorporated herein by reference in its entirety. Further, this application claims priority from Japanese Patent Application No. 2016-183781, filed Sep. 21, 2016, the disclosure of which is incorporated herein by reference in its entirety.

BACKGROUND OF THE INVENTION

1. Field of the Invention

The present invention relates to a measuring device that measures the morphology of a convex portion, such as a tumor formed on the skin of, for example, an animal.

2. Description of the Related Art

In the related art, for example, a method including forming a tumor on the skin of a small animal, such as a mouse, putting a candidate compound into the tumor, and observing a reduction in the size of the tumor to evaluate a drug effect has been performed in the research and development of, for example, an anticancer drug.

In a case where a reduction in the size of the tumor is to be observed as described above, the size of the tumor has been measured using, for example, a measuring equipment, such as a vernier caliper. However, it is difficult to fix the measuring equipment, such as a vernier caliper, to the tumor since the skin of the mouse is soft. Further, a method of fixing the vernier caliper to the tumor by an operator varies. For this reason, it is difficult to obtain objective measurement results.

A so-called three-dimensional scanner, which irradiates a tumor with light and measures the three-dimensional morphology of the tumor by detecting reflected light reflected from the tumor, is proposed in, for example, US2005/0084176A.

SUMMARY OF THE INVENTION

However, the three-dimensional scanner disclosed in US2005/0084176A also has a problem that the same measurement results are not obtained according to a method of disposing a mouse and the range of the tumor to be irradiated with light even though the same tumor is measured.

Further, in a case where a reduction in the size of the tumor is to be evaluated, the size of the tumor needs to be measured plural times in time series. However, since a method of disposing the mouse is performed or a range to be irradiated with light is set whenever the size of the tumor is measured, sufficient measurement accuracy cannot be obtained.

The invention has been made in consideration of the above-mentioned problem, and an object of the invention is to provide a measuring device that can measure the morphology of a convex portion, such as a tumor formed on the skin of an animal, with high accuracy.

A measuring device of the invention comprises a measuring unit that measures the morphology of a convex portion, and a position fixing unit that includes an opening in which the convex portion is to be disposed and a fixing member which includes the opening at a center thereof and against which a periphery of the convex portion is to be pressed. A size of the opening of the position fixing unit is capable of being changed.

Further, in the measuring device of the invention, the fixing member may be provided with a stop mechanism that changes the size of the opening.

Furthermore, in the measuring device of the invention, it is preferable that the fixing member has a shape of a ring.

Moreover, in the measuring device of the invention, it is preferable that stiffness of at least a portion of the fixing member against which the periphery of the convex portion is to be pressed is capable of being changed.

Further, in the measuring device of the invention, it is preferable that a resin member is provided on the portion of the fixing member against which the periphery of the convex portion is to be pressed and a plurality of the resin members having different stiffness are adapted to be interchangeable.

Furthermore, in the measuring device of the invention, it is preferable that a maximum length of the opening of the position fixing unit is in the range of 1 mm to 10 cm.

Moreover, in the measuring device of the invention, the measuring unit may set a base level on the basis of the fixing member and measure the morphology of the convex portion using the base level.

Further, in the measuring device of the invention, the measuring unit may set a surface of the fixing member, against which the periphery of the convex portion is to be pressed, as the base level.

Furthermore, the measuring device of the invention may further comprise a display control unit that acquires information about the morphology of the convex portion measured in time series by the measuring unit and displays the information about the morphology on the same screen or a plurality of screens so that the information about the morphologies are arranged in time series.

Moreover, in the measuring device of the invention, the display control unit may display numerical data as the information about the morphology of the convex portion so that the numerical data are arranged in time series.

Further, in the measuring device of the invention, the display control unit may display three-dimensional images of the convex portion as the information about the morphology of the convex portion so that the three-dimensional images of the convex portion are arranged in time series.

Furthermore, in the measuring device of the invention, the display control unit may display the three-dimensional images of the convex portion so that the three-dimensional images are aligned in a preset direction of the convex portion, in a case where the display control unit is to display the three-dimensional images of the convex portion so that the three-dimensional images of the convex portion are arranged in time series.

Moreover, in the measuring device of the invention, the display control unit may display information about the morphology of the convex portion, which are measured under different conditions, on the same screen or a plurality of screens so that the information about the morphologies of the convex portion are arranged in time series.

Further, in the measuring device of the invention, the measuring unit may irradiate the convex portion with light and measure the morphology of the convex portion by detecting reflected light reflected from the convex portion or light emitted from the convex portion.

Furthermore, in the measuring device of the invention, the measuring unit may scan the convex portion with laser light and detect reflected light reflected from the convex portion or light emitted from the convex portion due to scanning using the laser light.

According to the measuring device of the invention, there is provided the position fixing unit that includes an opening in which the convex portion is to be disposed and a fixing member which includes the opening at a center thereof and against which the periphery of the convex portion is to be pressed. Accordingly, even in a case where an object to be measured is a soft mouse or the like, the disposition of the convex portion, such as a tumor, can be stabilized. Further, since the size of the opening of the position fixing unit is capable of being changed, it is possible to stably measure the tumor by changing the size of the opening according to the size of the tumor even in a case where a tumor of which the size is changed with the lapse of time is to be measured. Accordingly, it is possible to measure the morphology of the convex portion with higher accuracy than in the related art.

DESCRIPTION OF THE PREFERRED EMBODIMENTS

Figure 1:
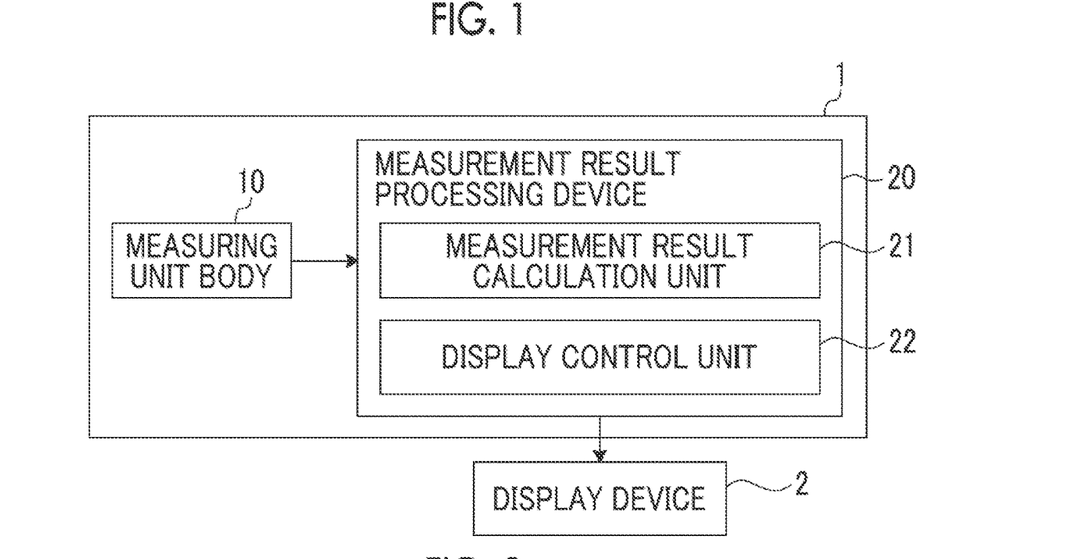
FIG. 1 is a block diagram showing the schematic configuration of a bioinstrumentation system that uses an embodiment of a measuring device of the invention.

A bioinstrumentation system, which uses an embodiment of a measuring device of the invention, will be described in detail below with reference to the drawings. FIG. 1 is a block diagram showing the schematic configuration of the bioinstrumentation system of this embodiment. The bioinstrumentation system of this embodiment measures the morphology of, for example, a convex portion, such as a tumor formed on the skin of an animal, and allows a display unit to display information about the morphology.

Figure 2:
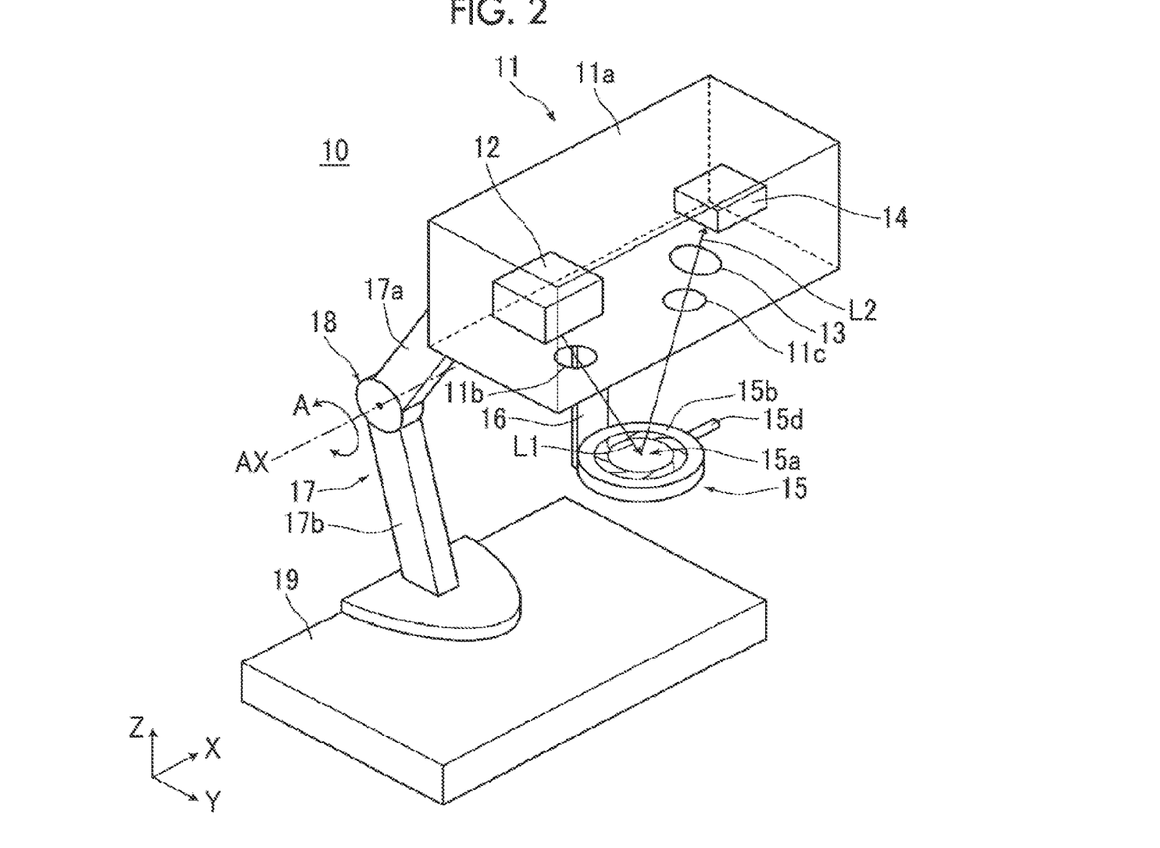
FIG. 2 is a diagram showing the schematic configuration of a measuring unit body shown in FIG. 1.

As shown in FIG. 1, the bioinstrumentation system of this embodiment comprises a measuring device 1 and a display device 2. The measuring device 1 comprises a measuring unit body 10 and a measurement result processing device 20. FIG. 2 is a diagram showing the specific configuration of the measuring unit body 10. In this embodiment, the measuring unit body 10 and a measurement result calculation unit 21 to be described later form a measuring unit of the invention.

As shown in FIG. 2, the measuring unit body 10 comprises a light detection unit 11, a position fixing unit 15, a light detection unit-support part 17, and a fixing base 19.

The light detection unit 11 comprises a light source unit 12, a condensing optical system 13, and a detection unit 14. The light source unit 12, the condensing optical system 13, and the detection unit 14 are received in a housing 11a. The housing 11a is formed of a member that blocks light, or the like. A through-hole 11b through which laser light L1 emitted from the light source unit 12 passes and a through-hole 11c through which reflected light L2 reflected from a convex portion as an object to be measured passes are formed in the housing 11a.

The light source unit 12 comprises a laser light source and a scanning mechanism that applies laser light L1 emitted from the laser light source. The convex portion fixed to the position fixing unit 15 is irradiated with laser light L1 emitted from the light source unit 12. Specifically, laser light L1 emitted from the laser light source is applied by the scanning mechanism, so that the surface of the convex portion is two-dimensionally scanned with laser light L1. A publicly known mechanism, which includes a mirror, an actuator, and the like, can be used as the scanning mechanism. A method of scanning the surface of the convex portion in directions orthogonal to each other with spot light or a method of scanning the surface of the convex portion in one direction with linear laser light L1 may be used as a method of two-dimensionally scanning the surface of the convex portion with laser light L1. In terms of measurement time, it is preferable that the surface of the convex portion is scanned in one direction with linear laser light L1. Further, the surface of the convex portion is scanned with laser light L1 in an X-Y plane shown in FIG. 2. A Z direction shown in FIG. 2 is a vertical direction, and the directions of an X-Y plane are horizontal directions.

The condensing optical system 13 condenses reflected light L2, which is reflected from the convex portion, on the detection unit 14. The condensing optical system 13 includes an optical element, such as a condensing lens.

The detection unit 14 detects the intensity of reflected light L2 that is reflected from the convex portion. For example, a charge-coupled device (CCD) image sensor, a complementary metal-oxide semiconductor (CMOS) image sensor, a line sensor, and the like can be used as the detection unit 14.

The position fixing unit 15 fixes the position of the convex portion as an object to be measured that is formed on the skin of an animal. Specifically, the position fixing unit 15 comprises an opening 15a in which the convex portion is to be disposed, and a fixing member 15b which includes the opening 15a at the center thereof and against which the periphery of the convex portion is to be pressed. The fixing member 15b is made of a black resin absorbing light, or the like, and is formed in the shape of a ring. The shape of a ring does not necessarily need to be a circular shape, and an opening 15a having a polygonal shape, such as a triangular shape and a quadrangular shape, may be formed.

The position fixing unit 15 is connected to the housing 11a of the measuring unit body 10 through a fixing unit-support member 16. One end of the fixing unit-support member 16 is connected to the position fixing unit 15, and the other end thereof is connected to the housing 11a. The length of the fixing unit-support member 16 in the vertical direction (the Z direction shown in FIG. 2) may be fixed, but it is more preferable that the length is variable.

Figure 3:
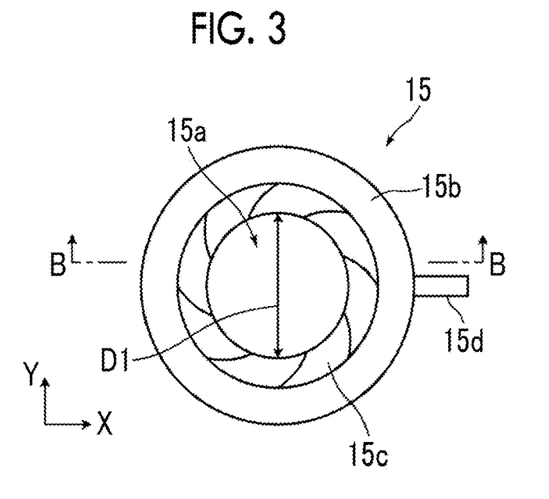
FIG. 3 is a top view of a position fixing unit.
Figure 4:
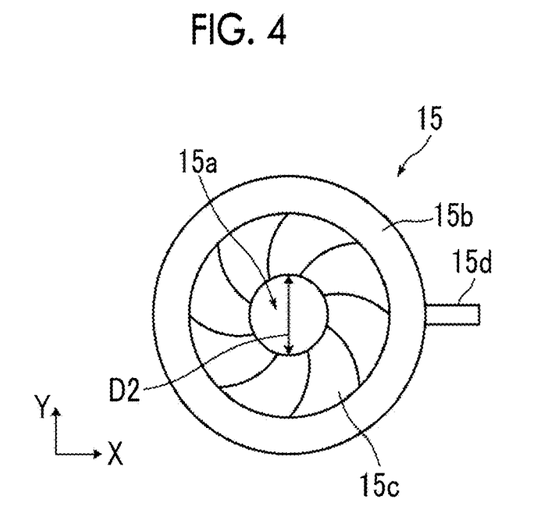
FIG. 4 is a top view of the position fixing unit.

FIGS. 3 and 4 are top views of the position fixing unit 15. As shown in FIGS. 3 and 4, the fixing member 15b of the position fixing unit 15 is provided with a stop mechanism 15c. The stop mechanism 15c changes the size of the opening 15a of the position fixing unit 15. FIG. 3 is a diagram showing a state where the stop mechanism 15c is adjusted so that the diameter of the opening 15a is set to D1. FIG. 4 is a diagram showing a state where the stop mechanism 15c is adjusted so that the diameter of the opening 15a is set to D2 (D1>D2). The position fixing unit 15 comprises an adjustment knob 15d that is used to adjust the size of the opening 15a formed by the stop mechanism 15c. A user operates the adjustment knob 15d according to the size of the convex portion, so that the stop of the stop mechanism 15c is adjusted and the size of the opening 15a is adjusted. It is preferable that the maximum diameter of the opening 15a is adjusted in the range of 1 mm to 10 cm.

The size of the opening 15a can be changed by the stop mechanism 15c in this embodiment, but the invention is not limited thereto. For example, a plurality of position fixing units 15 of which the sizes of the openings 15a are different from each other may be adapted to be attachable to and detachable from the fixing unit-support member 16.

Figure 5:
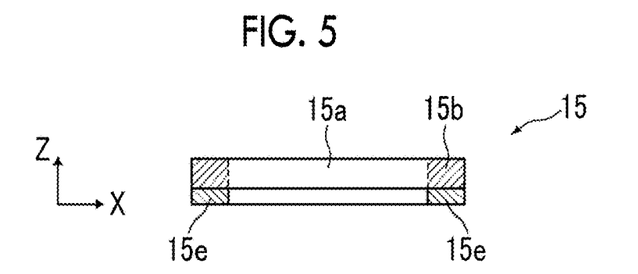
FIG. 5 is a side cross-sectional view of the position fixing unit.

Further, as shown in FIG. 5, the position fixing unit 15 comprises a silicone resin member 15e. FIG. 5 is a cross-sectional view of the position fixing unit 15 shown in FIG. 3 taken along line B-B. The stop mechanism 15c is not shown in FIG. 5. The silicone resin member 15e is provided on the lower surface of the fixing member 15b, that is, the surface of the fixing member 15b against which the periphery of the convex portion is to be pressed. The silicone resin member 15e is provided to allow the position fixing unit 15 to be in close contact with the skin of the periphery of the convex portion and to prevent damage to the skin of the periphery of the convex portion. The silicone resin member 15e has the same shape as the fixing member 15b, and is provided along the fixing member 15b.

Figure 6:
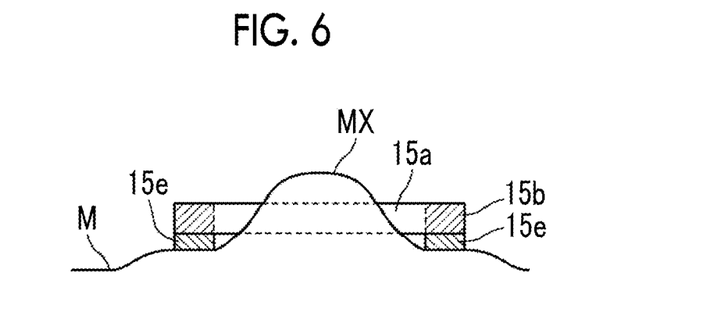
FIG. 6 is a side cross-sectional view showing a state where a convex portion is disposed in an opening of the position fixing unit.

The silicone resin member 15e is not limited to one type, and it is preferable that a plurality of silicone resin members 15e having different stiffness are adapted to be interchangeable. Specifically, a mounting portion may be provided on, for example, the lower surface of the fixing member 15b and a plurality of silicone resin members 15e having different stiffness may be adapted to be capable of being mounted on the mounting portion while being interchanged. For example, an adhesive layer to which the silicone resin member 15e can attachably and detachably adhere may be formed as the mounting portion, or a frame body to which the silicone resin member 15e can be attachably and detachably fitted may be formed as the mounting portion. Accordingly, for example, a silicone resin member 15e having low stiffness can be used in a case where the skin of a mouse is soft, and a silicone resin member 15e having high stiffness can be used in a case where the skin of the mouse is hard. Therefore, damage to the skin of the mouse can be prevented. FIG. 6 is a diagram showing a state where the silicone resin member 15e is pressed against a skin M of a mouse and a convex portion MX is disposed in the opening 15a. The stop mechanism 15c is not shown even in FIG. 6.

Silicone resin members 15e having different stiffness are adapted to be interchangeable in this embodiment, so that the stiffness of the position fixing unit 15 can be changed. However, the invention is not limited thereto, and, for example, a plurality of position fixing units 15 including fixing members 15b having different stiffness may be adapted to be attachable to and detachable from the fixing unit-support member 16.

Returning to FIG. 2, the light detection unit-support part 17 is connected to the light detection unit 11 and the fixing base 19 and supports the light detection unit 11 with respect to the fixing base 19. Specifically, the light detection unit-support part 17 comprises a first support part 17a of one end is connected to the light detection unit 11, a rotational moving part 18 to which the other end of the first support part 17a is connected, and a second support part 17b of which one end is connected to the rotational moving part 18. The rotational moving part 18 is adapted to allow the first support part 17a to be movable rotationally about a rotational movement axis AX in the direction of an arrow A. Accordingly, the height of the light detection unit 11 can be adjusted. The fixing base 19 having the shape of a rectangular parallelepiped is connected to the other end of the second support part 17b.

Returning to FIG. 1, the measurement result processing device 20 will be described. The measurement result processing device 20 is formed of a computer that comprises a central processing unit (CPU), a memory, and the like, and controls the entire bioinstrumentation system. The measurement result processing device 20 is a device where a measurement program is installed on a computer, and the respective components of the measurement result processing device 20 function in a case where the CPU operates the program. The measurement program is recorded in recording mediums, such as a digital versatile disc (DVD) and a compact disc read only memory (CD-ROM), and is distributed, and is installed on the computer from the recording medium. Alternatively, the measurement program is stored in a storage of a server computer, which is connected to a network, or a network-attached storage in a state where a user can access the measurement program from the outside; and is downloaded and installed on the computer on demand.

As shown in FIG. 1, the measurement result processing device 20 comprises a measurement result calculation unit 21 and a display control unit 22. The measurement result calculation unit 21 acquires a detection signal output from the detection unit 14 of the measuring unit body 10, and calculates the morphological information of the convex portion, which is formed on the skin of the animal, on the basis of the detection signal.

Specifically, the measurement result calculation unit 21 calculates the position of each scanning point of the convex portion by using, for example, a triangulation method or the like on the basis of the detection signal output from the detection unit 14. Then, the measurement result calculation unit 21 calculates the height of each scanning point of the convex portion on the basis of the position of each scanning point of the convex portion.

Figure 7:
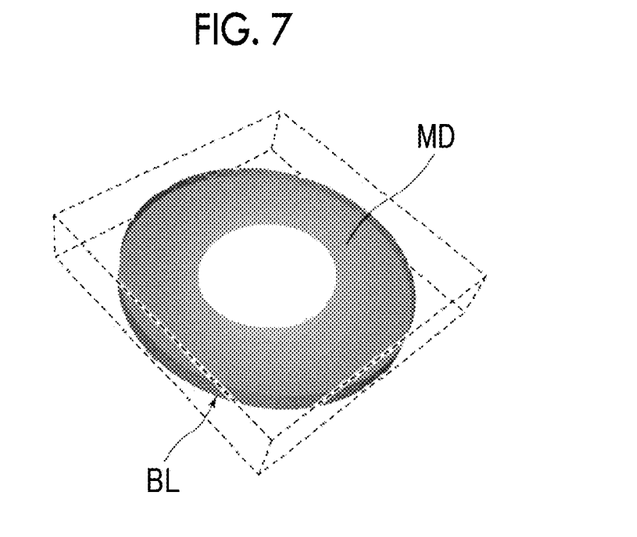
FIG. 7 is a diagram showing a three-dimensional model MD of a fixing member and a base level BL set on the three-dimensional model.

Here, in a case where the measurement result calculation unit 21 calculates the height of each scanning point of the convex portion, the measurement result calculation unit 21 sets a base level that is the reference of a height. The measurement result calculation unit 21 of this embodiment sets the lower surface of the fixing member 15b, that is, the surface of the fixing member 15b against which the periphery of the convex portion is to be pressed, as the base level. FIG. 7 is a diagram showing a three-dimensional model MD of the fixing member 15b and the base level BL set on the three-dimensional model. The three-dimensional model MD of the fixing member 15b shown in FIG. 7 is preset in the measurement result calculation unit 21 together with the three-dimensional position information thereof. For example, whenever the position of the lower surface of the fixing member 15b is changed due to the exchange of the position fixing unit 15 or a change in the length of the fixing unit-support member 16 in the Z direction, the position information of the three-dimensional model MD of the fixing member 15b is updated. Since the lower surface of the fixing member 15b is set as the base level as described above, the base level can be always set to the same position even in a case where, for example, a tumor is measured plural times in time series. The lower surface of the fixing member 15b is set as the base level in this embodiment, but the invention is not limited thereto. For example, the upper surface of the fixing member 15b or the middle plane of the fixing member 15b in the Z direction may be set as the base level.

Figure 8:
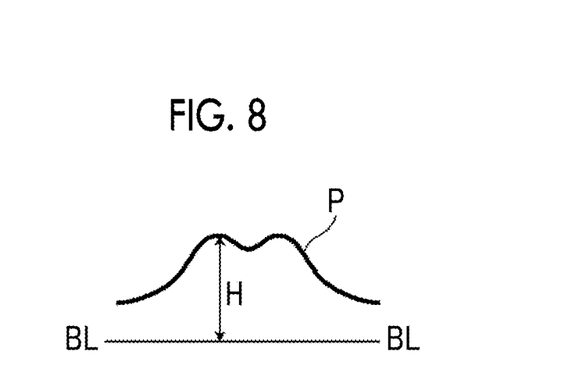
FIG. 8 is a diagram illustrating a method of acquiring the height of each scanning point of the convex portion.
Figure 9:
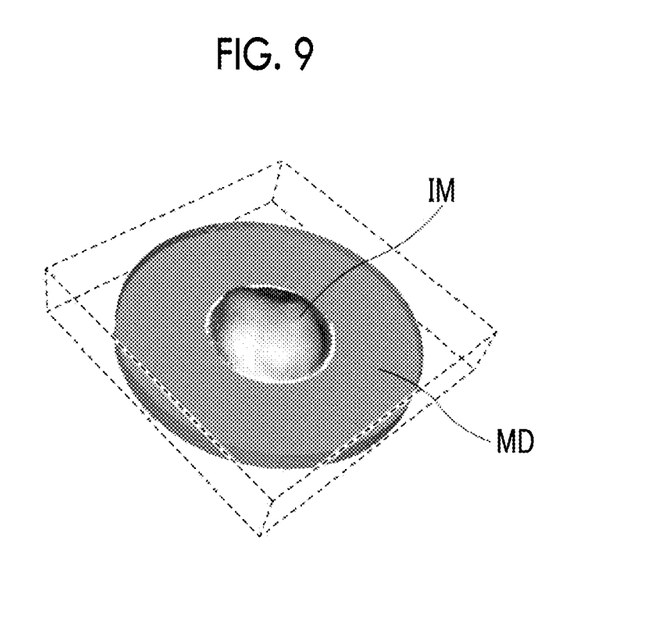
FIG. 9 is a diagram showing the three-dimensional model MD of the fixing member and a three-dimensional image IM of the convex portion.

Then, the measurement result calculation unit 21 acquires the height H of each scanning point of the convex portion by calculating a difference between the position P of each scanning point of the convex portion and the base level BL as shown in FIG. 8. FIG. 9 is a diagram showing the three-dimensional model MD of the above-mentioned fixing member 15b and a three-dimensional image IM of the convex portion that is calculated using the height H of each scanning point of the convex portion. The three-dimensional image IM of the convex portion is generated in a case where a polygonal surface is set using, for example, the height H of each scanning point of the convex portion. Various methods, which are publicly known, can be used as a method of generating the three-dimensional image IM of the convex portion.

Figure 10:
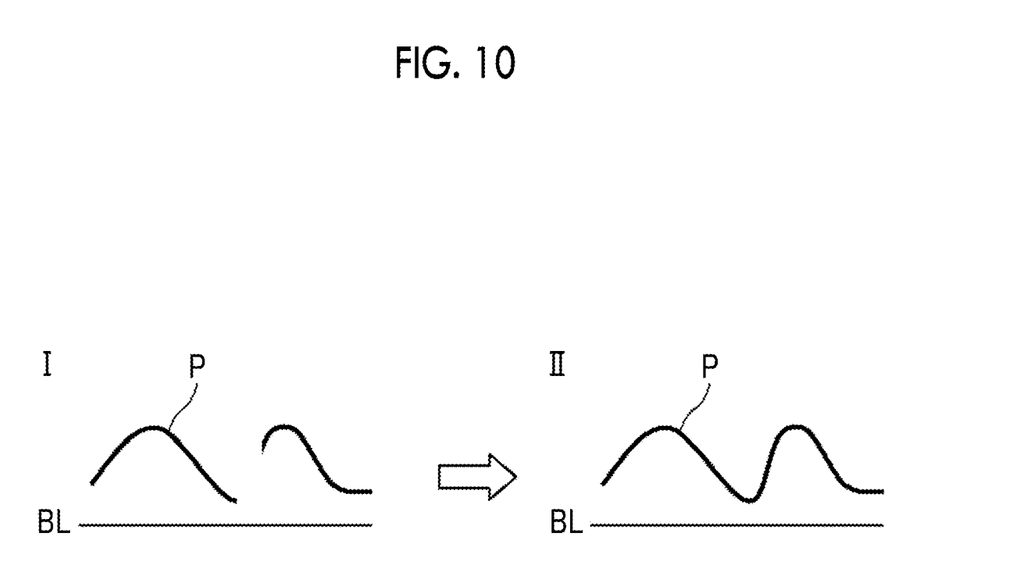
FIG. 10 is a diagram illustrating the interpolation of a measurement result.

For example, in a case where a tumor of a mouse has one convex portion, a case where a tumor of a mouse has an uneven shape having two convex portions, and the like, there is a case where positions P of scanning points of a part of a concave portion cannot be measured since a part of the concave portion cannot be irradiated with laser light L1 as shown in (I) of FIG. 10. In this case, as shown in (II) of FIG. 10, the positions P of the scanning points, which cannot be measured, may be acquired by interpolation calculation performed using the measured positions P of scanning points around the concave portion.

Further, the measurement result calculation unit 21 not only generates three-dimensional images as the morphological information of the convex portion but also calculates the volume, area, length, and the like of the convex portion using the three-dimensional images. For example, the maximum area of the area of the cut surface of the convex portion in a plane orthogonal to the Z direction may be calculated as the area of the convex portion. Furthermore, for example, the maximum length of the above-mentioned cut surface may be calculated as the length of the convex portion. The three-dimensional images of the convex portion, which are generated by the measurement result calculation unit 21, and the volume and the like of the convex portion are output to the display control unit 22.

The display control unit 22 allows the display device 2 to display morphological information, such as the three-dimensional images and the volume of the convex portion. Morphological information, such as the volume of the convex portion, may be displayed as numerical data, or may be displayed as a graph.

Figure 11:
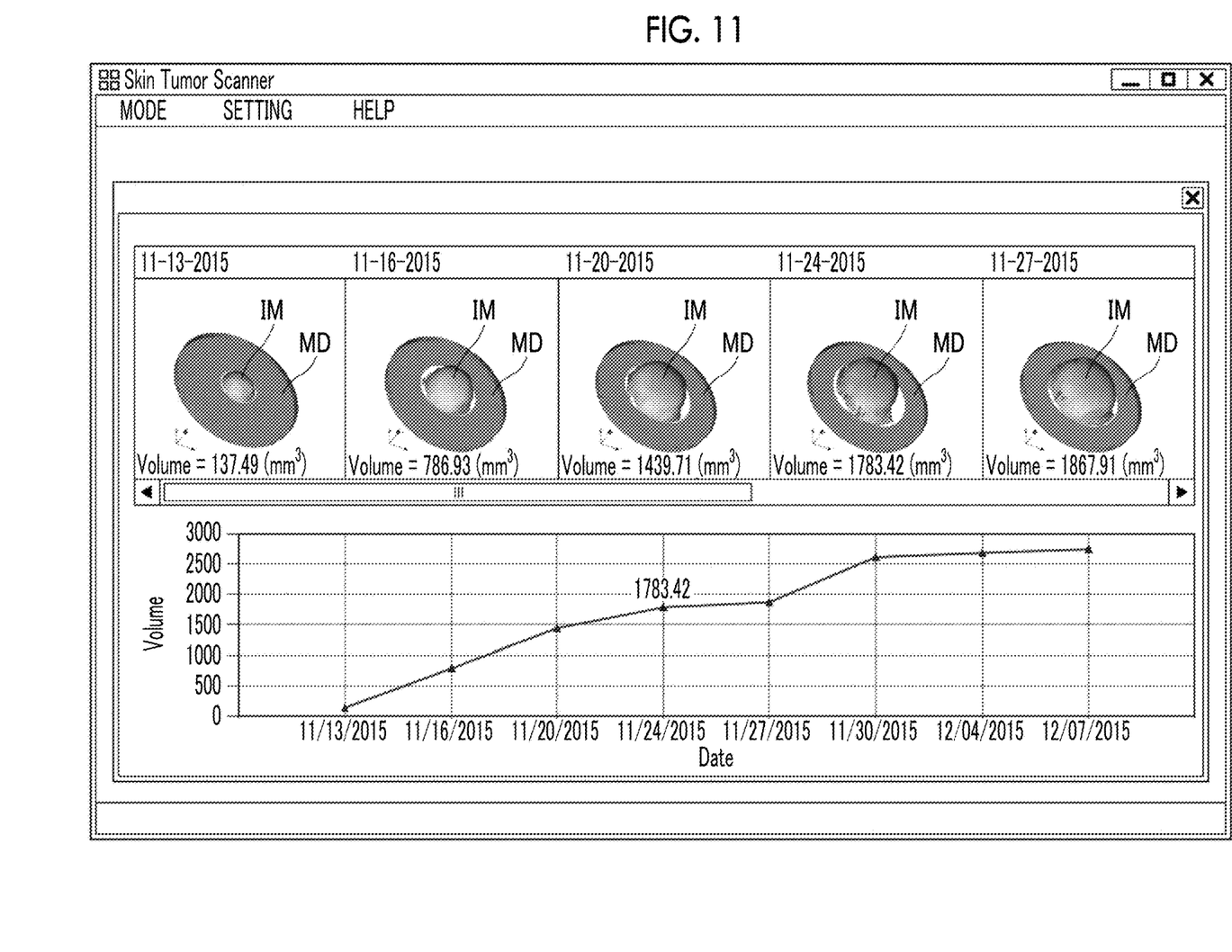
FIG. 11 is a diagram showing an example of a display method in a case where pieces of the morphological information of a convex portion of a mouse are measured in time series.

FIG. 11 is a diagram showing an example of a display method in a case where pieces of the information about the morphology of a convex portion of a mouse are measured in time series. It is preferable that the display control unit 22 acquires the morphological information of the convex portion measured in time series and displays the morphological information on the same screen or a plurality of screens so that pieces of the morphological information are arranged in time series. FIG. 11 is a diagram showing an example where results measured eight times in time series from a first measurement performed on Nov. 13, 2015 are displayed on the same screen. In FIG. 11, the three-dimensional images of the convex portion and the graph of the volume of the convex portion are displayed as morphological information. Only measurement results measured five times are displayed in regard to the three-dimensional images of the convex portion, but the other three measurement results measured three times can be displayed in a case in which a scroll bar displayed below the display columns for a three-dimensional image is operated to the right side.

Further, in a case where the three-dimensional images of the convex portion are to be displayed so as to be arranged in time series as shown in FIG. 11, it is preferable that the three-dimensional images are displayed so as to be aligned in a preset direction of the convex portion. For example, the direction of a major axis and the direction of a minor axis, in a case where the convex portion is approximated to an ellipse, can be set as the preset direction. Alternatively, the direction of the maximum length of each convex portion may be set as the preset direction. In a case where the display directions of the plurality of three-dimensional images of the convex portions are aligned as described above, it is possible to easily compare and observe the three-dimensional images. The display directions of the three-dimensional images of the convex portions may be adapted to finely adjustable according to inputs received from an input device (not shown), such as a mouse or a keyboard. Accordingly, it is possible to finely adjust the display directions of the three-dimensional images of the convex portions so that a user easily compares and observes the three-dimensional images.

Further, in a case where pieces of the morphological information of the convex portion measured in time series are to be simultaneously displayed on the same screen so as to be arranged as shown in FIG. 11, it is preferable that pieces of the morphological information of the convex portion measured under different conditions are further displayed on the same screen or a plurality of screens so as to be arranged in time series. Specifically, for example, the morphological information of the convex portion measured in time series in each of different periods of time may be displayed on the same screen or a plurality of screens so as to be arranged in time series. Alternatively, a plurality of pieces of morphological information, which are obtained in a case where a drug, such as an anticancer drug, is put into the convex portion (tumor) and the convex portion is measured in time series, and a plurality of pieces of morphological information, which are obtained in a case where a drug is not put into the convex portion and the convex portion is measured in time series, may be displayed on the same screen or a plurality of screens. Further, as the different conditions, different kinds of drugs may be put into the convex portion and different amounts of drug may be put into the convex portion. In a case where the morphological information of the convex portion measured under different conditions is displayed on the same screen or a plurality of screens as described above, information about the effect and the like of an anticancer drug can be obtained.

In the embodiment, the convex portion, such as a tumor, is irradiated with light and reflected light reflected from the convex portion is detected to measure the morphological information of the convex portion. However, light to be detected is not limited to the reflected light, and, for example, fluorescence emitted from the convex portion due to the irradiation of the convex portion with light may be detected to measure the morphological information of the convex portion.

EXPLANATION OF REFERENCES

1: measuring device
2: display device
10: measuring unit body
11: light detection unit
11a: housing
11b: through-hole
11c: through-hole
12: light source unit
13: condensing optical system
14: detection unit
15: position fixing unit
15a: opening
15b: fixing member
15c: stop mechanism
15d: adjustment knob
15e: silicone resin member
16: fixing unit-support member
17: light detection unit-support part
17a: first support part
17b: second support part
18: rotational moving part
19: fixing base
20: measurement result processing device
21: measurement result calculation unit
22: display control unit
AX: rotational movement axis
BL: base level
IM: three-dimensional image
L1: laser light
L2: reflected light
M: skin
MD: three-dimensional model
MX: convex portion
P: position of each scanning point of convex portion

What is claimed is:

1. A measuring device comprising:
a measuring unit including a sensor that measures a morphology of a convex portion; and
a position fixing unit that includes an opening in which the convex portion is to be disposed and a fixing member which includes the opening at a center thereof and against which a periphery of the convex portion is to be pressed,
wherein a size of the opening of the position fixing unit is capable of being changed, and the fixing member is provided with an iris diaphragm mechanism that changes the size of the opening,
wherein stiffness of at least a portion of the fixing member against which the periphery of the convex portion is to be pressed is capable of being changed, and
wherein a resin member is provided on the portion of the fixing member against which the periphery of the convex portion is to be pressed, and a plurality of resin members, including the resin member, having different stiffness are adapted to be interchangeable.

2. The measuring device according to claim 1,
wherein the fixing member has a shape of a ring.

3. The measuring device according to claim 1,
wherein a maximum length of the opening of the position fixing unit is in a range of 1 mm to 10 cm.

4. The measuring device according to claim 1, further comprising:
a processor configured to set a measurement corresponding to the fixing member as the base level and measures the morphology of the convex portion using the base level.

5. The measuring device according to claim 4,
wherein the processor is further configured to set a measurement corresponding to a surface of the fixing member, against which the periphery of the convex portion is to be pressed, as the base level.

6. The measuring device according to claim 1, further comprising:
a display controller configured to acquire information about the morphology of the convex portion measured in time series and display the information about the morphology on one screen or a plurality of screens so that the information about morphologies are arranged in time series on a display device.

7. The measuring device according to claim 6,
wherein the display controller is further configured to display numerical data as the information about the morphology of the convex portion so that the numerical data are arranged in time series.

8. The measuring device according to claim 6,
wherein the display controller is further configured to display three-dimensional images of the convex portion as the information about the morphology of the convex portion so that the three-dimensional images of the convex portion are arranged in time series.

9. The measuring device according to claim 8,
wherein the display controller is further configured to display the three-dimensional images of the convex portion so that the three-dimensional images are aligned in a preset direction of the convex portion, in a case where the display controller is to display the three-dimensional images of the convex portion so that the three-dimensional images of the convex portion are arranged in time series.

10. The measuring device according to claim 6,
wherein the display controller is further configured to information about the morphology of the convex portion, which are measured under different conditions, on one screen or a plurality of screens so that the information about the morphologies of the convex portion are arranged in time series.

11. The measuring device according to claim 1,
wherein the measuring unit further includes a light source that irradiates the convex portion with light and measures the morphology of the convex portion by detecting reflected light reflected from the convex portion or light emitted from the convex portion.

12. The measuring device according to claim 11,
wherein the measuring unit includes a scanner that scans the convex portion with laser light and detects reflected light reflected from the convex portion or light emitted from the convex portion due to the scanning using the laser light.

* * * * *